(12) United States Patent
Finger et al.

(10) Patent No.: US 7,579,039 B2
(45) Date of Patent: Aug. 25, 2009

(54) COATING AN INTERDENTAL CLEANING REGION OF AN INTERDENTAL CLEANING DEVICE

(75) Inventors: Gerhard Finger, Schmitten (DE); Thorsten Emge, Rodgau (DE); Manfred Klawuhn, Frankfurt am Main (DE)

(73) Assignee: Braun GmbH, Kronberg (DE)

( * ) Notice: Subject to any disclaimer, the term of this patent is extended or adjusted under 35 U.S.C. 154(b) by 326 days.

(21) Appl. No.: 10/558,161

(22) PCT Filed: May 18, 2004

(86) PCT No.: PCT/EP2004/005324

§ 371 (c)(1),
(2), (4) Date: May 30, 2006

(87) PCT Pub. No.: WO2004/103204

PCT Pub. Date: Dec. 2, 2004

(65) Prior Publication Data

US 2006/0249174 A1    Nov. 9, 2006

(30) Foreign Application Priority Data

May 23, 2003 (DE) .................................. 103 23 328

(51) Int. Cl.
*A61C 15/04* (2006.01)
(52) U.S. Cl. .................. 427/2.29; 132/329; 132/323; 132/321; 132/325; 132/91; 424/443; 428/372; 428/375; 428/378; 428/394; 264/229; 264/251; 427/2.1; 427/430.1

(58) Field of Classification Search ............... 132/323, 132/321, 91, 329; 424/443; 428/372; 264/229; 427/2.29
See application file for complete search history.

(56) References Cited

U.S. PATENT DOCUMENTS

| 3,672,378 | A | | 6/1972 | Silverman |
| 4,029,113 | A | * | 6/1977 | Guyton .................. 132/321 |
| 4,034,771 | A | | 7/1977 | Guyton |
| 4,911,927 | A | * | 3/1990 | Hill et al. .................. 424/443 |
| 5,284,169 | A | | 2/1994 | Gilligan et al. |
| 5,357,990 | A | | 10/1994 | Suhonen et al. |
| 5,680,876 | A | * | 10/1997 | Hasham et al. ............ 132/329 |
| 6,080,481 | A | * | 6/2000 | Ochs et al. ................ 428/372 |
| 6,544,457 | B1 | * | 4/2003 | Rieser .................... 264/229 |

FOREIGN PATENT DOCUMENTS

| DE | 44 39 931 | 9/1996 |
| DE | 299 03 413 | 8/1999 |
| DE | 198 34 247 | 3/2000 |
| EP | 0 707 836 | 4/1996 |

\* cited by examiner

*Primary Examiner*—Michael Barr
*Assistant Examiner*—Andrew Bowman
(74) *Attorney, Agent, or Firm*—Fish & Richardson P.C.

(57) ABSTRACT

A method for coating a cleaning region of an interdental cleaning device, which includes preheating the cleaning region to a predetermined temperature. Then, immersing the preheated cleaning region in a coating agent. The coating agent including a flavoring agent encapsulated in a wax, thereby forming a coating on the cleaning region upon immersion. Next, a flow of air is forced across the coated cleaning region in a drip zone, thereby removing an excess portion of the wax and exposing at least a portion of the flavoring agent at a surface of the coating. Then, the coating is cured by cooling the cleaning region.

14 Claims, 6 Drawing Sheets

COATING AN INTERDENTAL CLEANING REGION OF AN INTERDENTAL CLEANING DEVICE

TECHNICAL FIELD

This description relates to coating an interdental cleaning region of an interdental cleaning device, e.g., the cleaning region of a dental pick or the dental side of a flosser or flossette (dental floss holder with a strand of dental floss secured between the free arms).

BACKGROUND

Interdental cleaning devices such as dental picks or dental floss coated with a flavoring agent are known in the art. In particular refreshing flavoring agents such as peppermint flavor, essential oils and other flavoring agents, e.g., lemon, strawberry or vanilla flavoring are suitable for this purpose. Thereby, in addition to the cleaning effect which is determined by the function of the dental pick, namely removing residues of food in the interdental spaces, an additional freshening effect in the oral cavity is achieved, and this is an important component of modern oral hygiene. The increased value for the user thereby made available is directly reflected in an increased wellbeing and more secure presentation in social discourse with other humans.

For example, a cleaning device of this type is described in German Utility Model DE 298 13 353 U1 which discloses a dental pick made of wood having a flavoring substance and a pleasant scent. The dental pick may also be coated with medicinal additives to prevent dental disease. Scents and flavoring agents that may be used here include orchid scent, banana, coffee, chocolate and strawberry flavoring and perfumes. The coating is applied to the tip of the dental picks by a roller which carries the corresponding coatings materials. The roller rolls over the tips of the dental picks and thereby applies the flavoring and aromatic substances. This method is based on the absorbency of the wooden dental picks. It is not possible, by this method, to apply a coating of uniform quality to dental picks made of plastic.

German Patent DE 198 34 247 A1 describes a dental pick made of wood or plastic, which for reasons of hygiene and to create an attractive dental pick is at least provided with a layer of a flavoring agent. Examples of coating methods proposed include dipping or vapor deposition. However, this type of coating is problematical with dental picks made of plastic because many plastics, e.g., polypropylene, can be wetted only after a complex hydrophilizing treatment.

The plastic dental pick proposed in German Patent DE 198 34 247 A1 has at least one axial capillary in which the dry residues of the liquid flavoring agent and additional additives can be stored for good and adequate application of flavoring agent. Furthermore, it is proposed that the coating shall consist of multiple layers consisting of flavoring agents, disinfectants and coloring agents. However, the proposed coating method for plastic dental picks has some disadvantages. First, a capillary must be created in the dental pick itself and secondly, the coating material is then not applied uniformly over the dental pick. Therefore, the flavoring agents are activated only with a considerable delay because they must first be released from the capillary by the saliva. In view of the relatively short use times for removing food residues from interdental spaces, this is a disadvantage and under some circumstances completely prevents the development of the flavor.

U.S. Pat. No. 3,926,201 and U.S. Pat. No. 4,006,750 describe methods for manufacturing flossers consisting of a handle and two arms extending away from the handle in the manner of a fork with a strand of dental floss stretched between the arms. The dental floss is inserted into an injection mold for fastening it in the arms of the flosser and when the flosser is molded by injecting plastic material into the injection mold, the strands of dental floss are surrounded by plastic so that the string of dental floss is securely anchored in the arms after the flosser is removed from the mold.

SUMMARY

According to one aspect, a method for coating interdental cleaning regions of an interdental cleaning device, such as dental picks or the dental floss of a flosser. Furthermore, in one embodiment a coating of uniform quality is to be achieved with the method, manifesting its effect within an extremely short period of time. Finally, in preferred embodiments the method should meet the prevailing valid hygiene standards in the manufacture of oral hygiene products. In another aspect, a dental pick and/or a flosser according to this method are also to be created.

In one embodiment, a method for coating interdental cleaning regions of an interdental cleaning device includes preheating the cleaning region to a predetermined temperature. Preferably, this is done in a sealed, heated and thermally regulated area. The temperature is preferably kept within the limits of 40° C. to 100° C. with an accuracy of ±5° C. The cleaning device remains in the preheating zone until it reaches the desired temperature. Infrared lamps are preferred over fans as the heat sources because with infrared lamps the risk of contamination due to air circulation is the lowest.

Following preheat, the cleaning region is immersed in an immersion bath container which is filled with a coating agent, which includes a flavoring agent encapsulated in a wax. A conveyor device, i.e., a conveyor track, may be employed to lift and lower the cleaning region into and out of the immersion bath container containing the coating agent. In doing so, the dwell time of the cleaning region in the immersion bath depends on the preheating temperature. For example, if the temperature of the interdental cleaning device is above the temperature of the coating liquid, then, preferably, the dwell time of the device in the immersion bath is the shortest. However, if the temperature of the device is lower than the temperature of the immersion bath, then, preferably, the heat transfer is taken into account. The action of lowering the device is coordinated to achieve a controllable and reproducible coating. The interdental cleaning device is lowered in such a way that at least the cleaning region is coated.

In a preferred embodiment, the immersion bath container circulates the coating agent, including between about 50% and about 75% paraffin wax, at a constant wax content. In some embodiments, the immersion bath container has double walls and is regulated by means of a thermostat in a temperature range from 60° C. to 90° C. with a tolerance of ±2° C., depending on the temperature. In some cases, the heated immersion bath container also has a free surface area which corresponds to a ground area of the conveyor rack and has a minimum depth which permits a desired coating thickness. Some embodiments may include an overflow which keeps the wax content constant is provided on the immersion bath container along with a circulating pump which prevents the encapsulated flavorings from settling out at the bottom. Furthermore, the immersion bath container may include heated jacketed water pipes between the tank and the pump which prevent waxy layers from being deposited on the pipe walls.

In accordance with such embodiments, the coating liquid is completely replaced at regular intervals to prevent oxidation and contamination.

Following immersion, a flow of heated air is forced across the cleaning region in a drip zone to remove excess wax and to expose at least a portion of the flavoring agent at the surface of the coating. The forced air may be filtered here for reasons of hygiene and is preferably heated to a temperature in the range of between about 90° C. and about 140° C.

Then, following the removal of wax and exposure of the flavoring agent, the cleaning region is cooled to allow the coating to harden.

According to some embodiments, the cleaning device is a dental pick having a clamping point at one end and a tip at another end. In the case of the dental pick, the cleaning region is a region adjacent to the tip. The wax at the surface of the coating of the cleaning region can be removed in an especially short period of time if the cleaning area is part of a dental pick which is directed at its tip downward in the direction of gravity. This is because small droplets can develop at the tip in particular and can easily be blown away by the forced air flow. The finer the tip of the dental pick, the more coating agent can be removed from the dental pick within an extremely short period of time.

In some embodiments, the cleaning device includes multiple dental picks attached to a common sprue web. Due to the fact that multiple dental picks are attached to a sprue web, a great many dental picks can be coated automatically by means of a conveyor device which automatically conveys multiple dental picks into the immersion bath container and out of it again in an especially short period of time.

In another embodiment, the cleaning device is a flosser having a handle with a pair of arms extending outwardly from the handle and forming a forked end with a strand of dental floss stretch between the arms, in which case the strand of dental floss spanning the two arms is immersed with the free ends of the arms into the coating agent to such an extent that at least the strand of dental floss is completely immersed. The handle connecting the two arms of the flosser serves as a suspension point or fastening point on a conveyor belt. After subsequent removal of the flossers from the immersion bath, excess wax is removed from the strand of dental floss by the forced air flow in the drip zone. The air flow is directed so that it is always directed at only one clamped point on the dental floss to ultimately convey a drop that is still adhering to the clamping point, if it does not already drop off, so that it can remain adhering there as excess material. It therefore does not cause any thickening in the central area of the dental floss, which would be undesirable. Since the air is blown against the coating surface, the wax is removed superficially at the surface of the dental floss and at least a portion of the flavoring agents are exposed at the surface and then are very rapidly released on insertion of the dental floss into an interdental space, thereby imparting a pleasant taste to an operating person.

According to some embodiments, the cleaning devices can be coated especially easily with the coating agent if they are made of plastic and at the same time have a temperature in the range of about 40° C. to about 100° C. In such embodiments, the temperature of the coating agent is preferably between about 70° C. and about 90° C. However, it is of course advantageous if both the cleaning device as well as the coating agent are at approximately the same temperature to ensure optimum adhesion of the liquid to the dental pick and/or to the dental floss.

According to another embodiment, the cleaning device is exposed to the air flow after being coated, whereby the air flow runs in the longitudinal direction toward the tip, in the case of a dental pick, and toward a fastening point, in the case of a flosser, to thereby ensure that the cleaning area does not have any droplet-shaped accumulations of excess wax. The air flow is heated, preferably between about 90° C. and about 140° C. This achieves the result that even with slight cooling of the coating, this drop in temperature is eliminated by the hot air flow. After most of the wax has been blown away from the surface of the coating, the cleaning device is preferably cooled to ambient temperature, which is usually sufficient to cause the coating to solidify.

In some embodiments, the coating agent is a mixture including the wax, the wax encapsulated flavoring agent, and a second flavoring agent in liquid form. Preferably, the coating agent contains between about 50 percent and about 75 percent paraffin wax; between about 20 percent and about 40 percent wax encapsulated flavoring agent; between about 2 percent and about 6 percent liquid flavoring agent; and between about 0.1 percent and 5 percent emulsifiers and antioxidants as additives, preferably BHT (2,6-di-tert-butyl-4-methylphenol).

In some embodiments, the coating agent is prepared in an agitator prior to immersing the cleaning region in the coating agent, the preparation including: First, heating an immersion bath container to about 100° C. Agitators that are generally known from the process engineering may be used here. Then paraffin wax blocks are placed in the preheated agitator and melted at a temperature of between about 80° C. and about 100° C. Microcrystalline paraffin wax approved for use with foods is suitable. Next, a liquid flavoring oil, preferably liquid peppermint oil, and a stabilizer and/or an antioxidant such as BHT (2,6-di-tert-butyl-4-methylphenol) is added with continuous agitation and stirred uniformly. An initially strong odor of peppermint is released when a package is opened and when a dental pick is used. Then encapsulated flavoring oils, preferably spray-dried peppermint flavoring, are added to the mixture and undermixed uniformly. The encapsulated flavoring oils do not manifest their flavoring until after they are dissolved in an aqueous liquid, i.e., in the mouth during use of a dental pick or a flosser, and they ensure a long-lasting flavoring. Therefore, the dental pick or flosser may also be inserted into multiple interdental spaces without permanently losing its flavoring. The dispersion, i.e., extremely fine distribution of the available flavoring oils in molten paraffin wax, is accomplished by using a homogenizer at a constant temperature of between about 75° C. and about 80° C. so that the wax and particles are constantly being mixed.

As soon as a homogeneous dispersion is obtained after testing, the resulting homogeneous coating liquid is transferred to the immersion bath container of an immersion bath device. The finished coating liquid hardens at room temperature. It can be applied to the surface of dental pick made of plastic or to the surface of dental floss made of polyamide [nylon] by the coating method described above in a coating thickness of 10 μm to 250 μm.

In another aspect, an interdental cleaning device cleaning region coating apparatus includes a preheating device for preheating the cleaning region; a heated immersion bath container disposed adjacent to the preheating device and containing a coating agent, the coating agent including a flavoring agent encapsulated in a wax; a time-controlled conveying device for immersing and retracting the cleaning region into and out of the coating agent; and a fan disposed along a conveyance path of the conveying device; and a heater for heating a flow of air forced by the fan across the cleaning region as conveyed along the conveyance path. This ensures that if the dental picks cool too rapidly after they are removed from the immersion bath, they will be kept at the proper temperature by a stream of hot air to keep the excess wax liquid and to remove this excess wax from the surface of the coating within a particularly short period of time. Using such an installation, many dental picks can be coated in a fully automatic process in which the surface of the coating agent is subsequently partially freed of wax by means of an air flow to expose at least a potion of the flavoring agents.

According to another aspect, a dental pick includes a clamping point at a first end, and a tip at an opposite end. The tip having a coating including between about 50 percent and about 75 percent paraffin wax; between about 20 percent and about 40 percent wax encapsulated flavoring agent; between about 2 percent and about 6 percent liquid flavoring agent; and between about 0.1 percent and 5 percent emulsifiers and antioxidants as additives. At least a portion of the flavoring agents are exposed at a surface of the coating substantially free of the wax.

In some embodiments, the dental pick is a plastic, preferably polypropylene.

According to yet another aspect, a flosser includes a handle and a pair of arms extending outwardly from the handle forming a forked end with a strand of dental floss stretch between the arms at the forked end. Such embodiment may include dental floss made of polyamide [nylon]. This material has an especially high tensile strength, while also having good friction properties and being especially suitable for cleaning the interdental spaces. This material can also be joined to the material of the arms, which along with the holder are preferably made of polypropylene, by the melting process especially well.

Additional embodiments and advantages of the present invention are explained by the following description of an exemplary embodiment with reference to the accompanying drawings, which show:

DESCRIPTION OF DRAWINGS

The same or similar parts are labeled with the same reference notation below.

DETAILED DESCRIPTION

Figure 1:
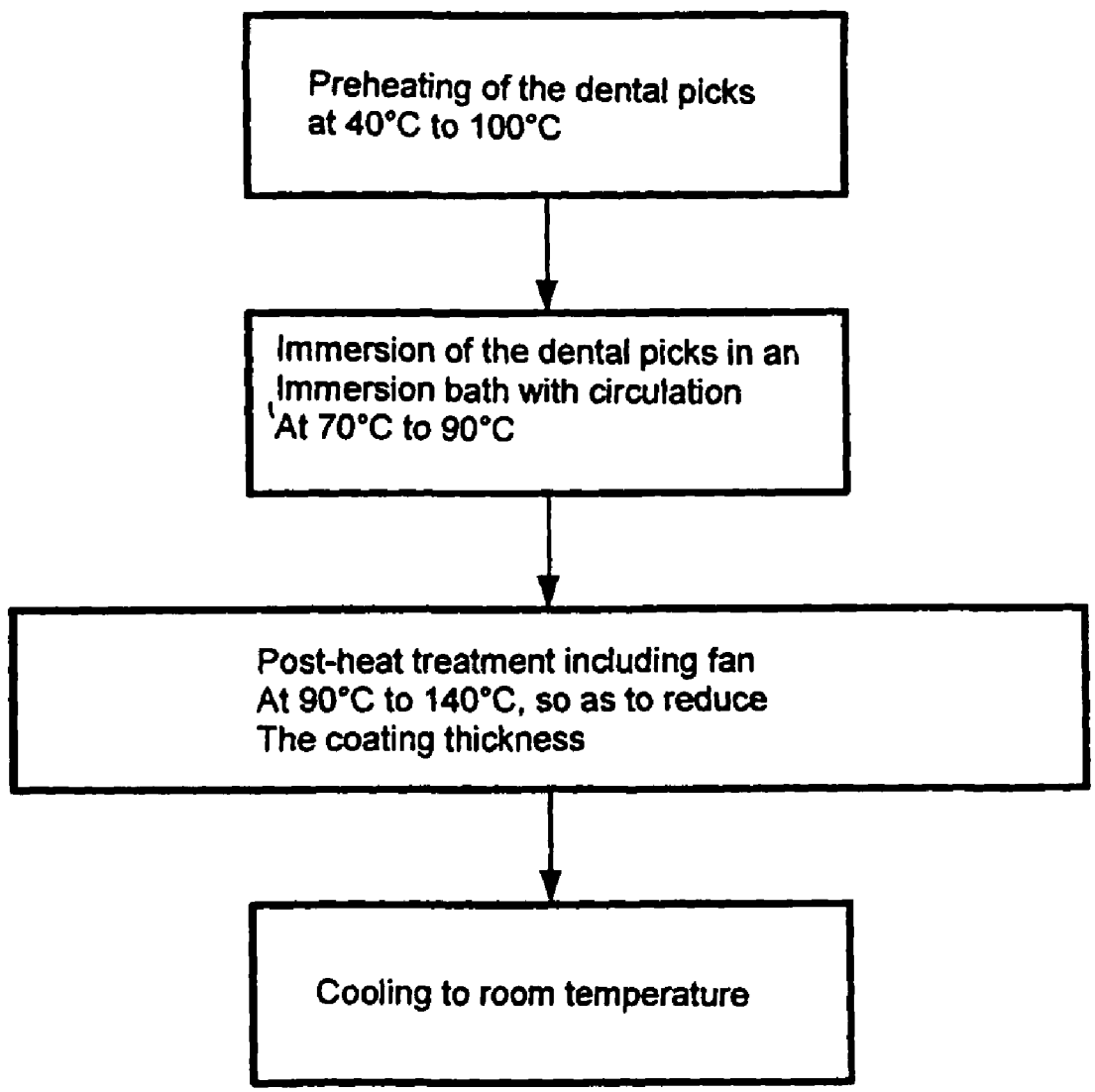
FIG. 1 a flow chart diagramming the coating method.
Figure 2:
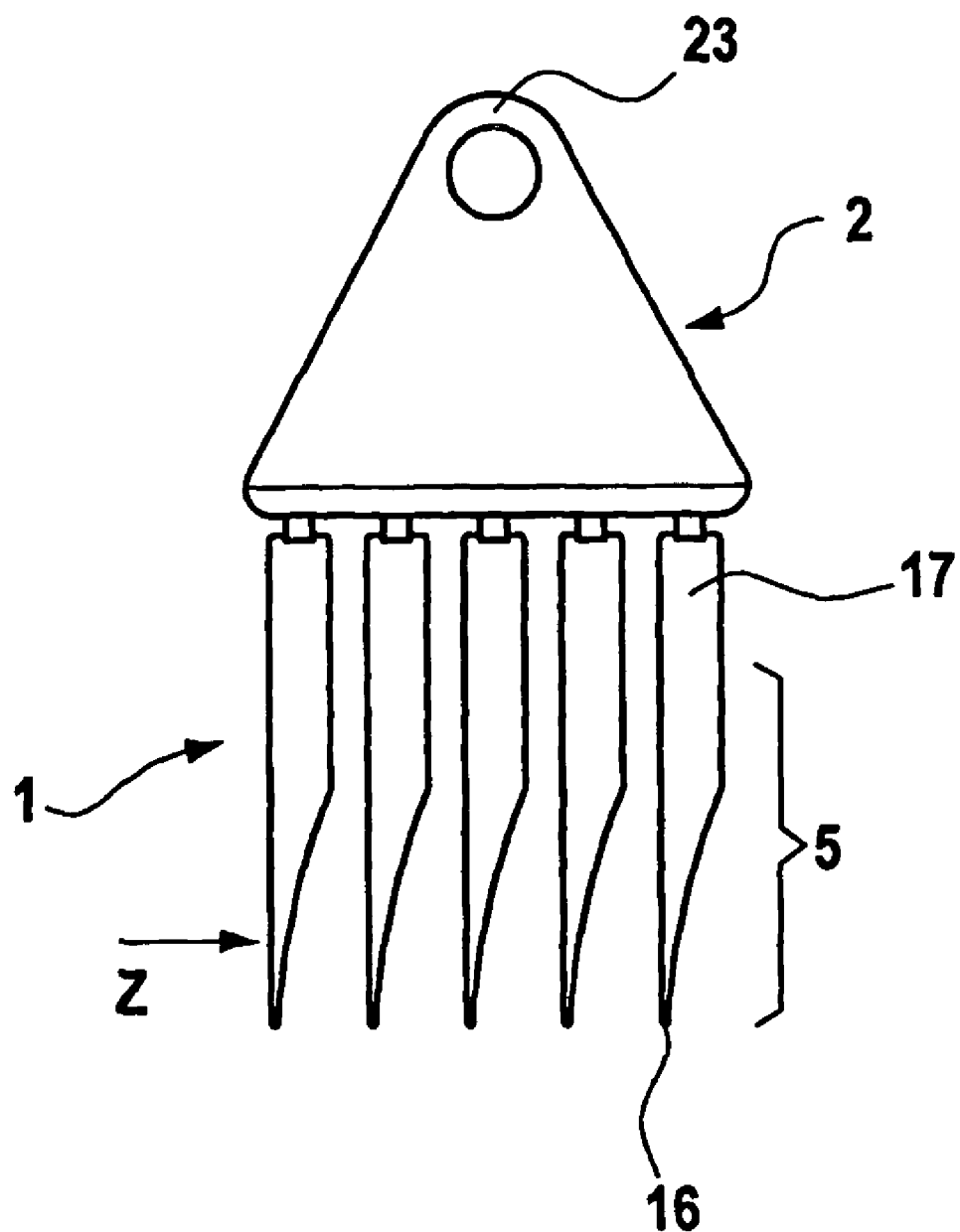
FIG. 2 a schematic view of plastic dental picks on a sprue web.
Figure 3:
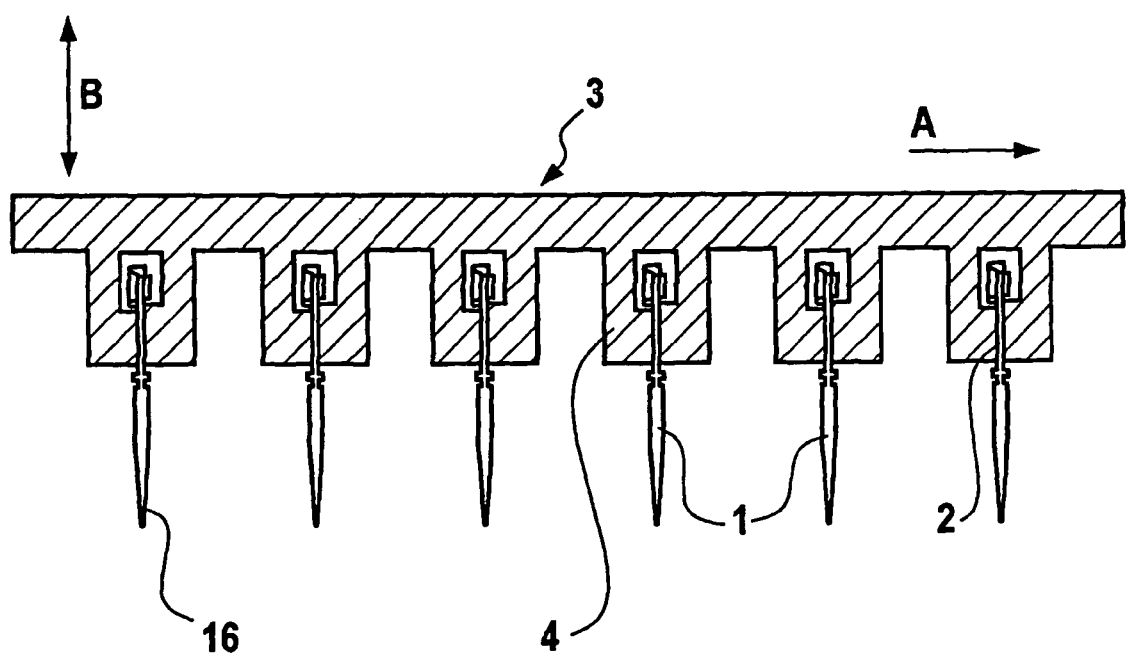
FIG. 3 a schematic diagram of a conveyor rack conveying the dental picks.
Figure 4:
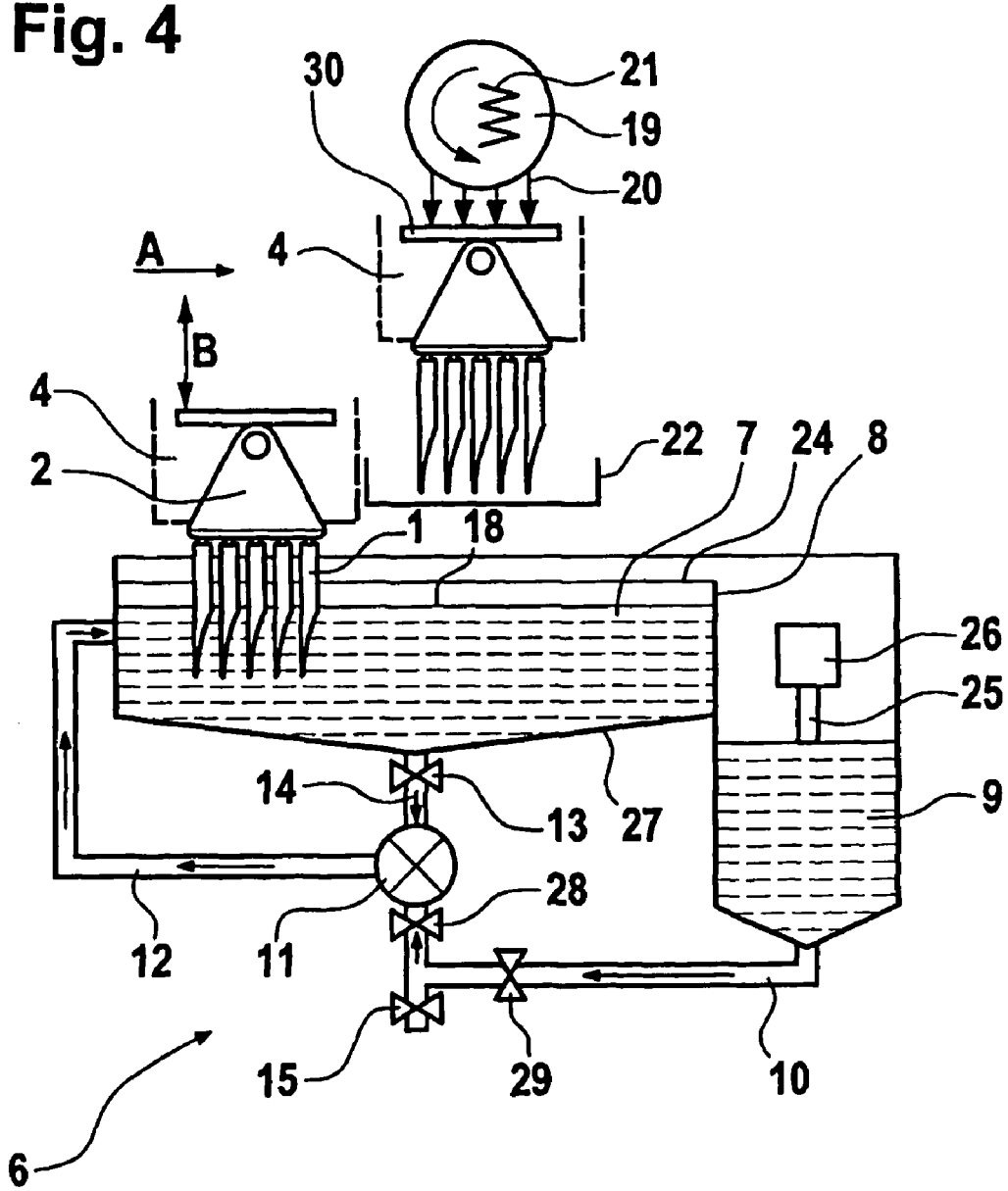
FIG. 4 a schematic diagram of a device for coating dental picks.

FIG. 1 shows a flow chart which diagrams a method for coating dental picks. The dental picks 1 are treated in different processing zones (FIGS. 2, 3, 4). The plastic dental picks are automatically conveyed by a conveyor rack 4 (FIG. 4) to the processing zones and are optionally also raised and lowered there as symbolized in FIG. 4 by the arrows used to indicate directions A and B of the conveyance, lifting and lowering device.

In performing the coating process, it is preferable that hygiene conditions double than those for working with food be maintained throughout the entire process and for the equipment required for it. This includes, among other things, that all machine parts coming in contact with the dental picks 1 be manufactured from materials approved for use with foods such as high grade steel, food grade plastics, etc. Furthermore, it is preferable that contamination due to dust or other dirt particles in the air be prevented by sealing off the system with respect to the environment. Furthermore, it is preferred that lubrication of the machine parts be done only by using food grade lubricant and that any dripping of lubricant or escape of fines from abrasion is prevented through appropriate encapsulation of the respective components.

Preheating of the dental picks 1, which are usually made of a thermoplastic by an injection molding process, is performed essentially to be able to better absorb the coating fluid which is based on microfine wax. FIG. 2 shows, as an example, a schematic view of five dental picks 1 made of a thermoplastic on a sprue 2 molded in a triangular shape, serving as the conveyance and connecting device as well as a means of handling for an operating person in separating a dental pick 1.

Experiments have shown that a preheating temperature of between about 40° C. and about 100° C. is especially favorable to improve the adhesion properties of the coating fluid 18 on the plastic surface of the dental picks 1. It is most advantageous if the preheating temperature of the dental picks 1 corresponds to the temperature of the coating fluid 18 (FIG. 4) in the immersion bath container 7 because this makes it possible to minimize the dwell time of the dental picks 1 in the immersion bath container 7.

FIG. 3 shows a schematic view of the conveyor rack 3 which accomplishes the automatic conveyance of the dental picks 1 from one processing zone to the next. The sprue pieces 2 with the dental picks 1 are arranged vertically in the sprue receptacles 4 of the conveyor rack 3, i.e., so they hang there, shown here in a side view. In the present exemplary embodiment, six rows of sprue pieces 2 are conveyed one after the other on the conveyor rack 3. Each row has five sprue pieces 2 each with five dental picks 1, i.e., in the present exemplary embodiment 150 dental picks 1 made of plastic can be conveyed simultaneously in the direction of arrows A and B (FIGS. 3, 4) and coated by the method according to this invention.

The dental picks 1 are arranged in such a way that the tips 16 of the dental picks point down, so that the force of gravity can be utilized in the individual processing steps and excess coating fluid 18 can drip down over the tips 16 of the dental picks. The triangular sprue webs 2 in the present exemplary embodiment are held with their pointed side 23 in the sprue receptacle 4 of the conveyor rack 3.

FIG. 4 shows, schematically, a device 6 for coating dental picks 1. The device 6 has an immersion bath container 7 with coating agent 18 in the form of a liquid. The dental picks 1 which are held on the sprue receptacle 4 (shown with dotted lines) with their sprue web 3 are lowered by means of a lifting, lowering and displacing device, indicated by arrows A and B, into the immersion bath container 7 until an intended area 5 is coated with the coating liquid 18 as shown in FIG. 2. The coating length of the cleaning area 5 in the present exemplary embodiment is preferably between about 17 mm and about 21 mm, measured from the tip 16 of the dental pick. During the coating operation in the present exemplary embodiment, a coating with a thickness of approximately 10 μm to 250 μm and a weight of approximately 5 mg to 50 mg per dental pick 1 is applied.

The immersion bath container 7 is designed so that it circulates the coating liquid 18 at a constant filling level to ensure optimum and thorough mixing of the coating liquid 18. To this end, the immersion bath container 7 is designed with double walls and is regulated by a thermostat (not shown) in a temperature range from 60° C. to 90° C. with an accuracy of ±2° C.

According to FIG. 4, the heated immersion bath container 7 has a free surface 24 which in the present exemplary embodiment corresponds at least to the rectangular base area of the conveyor rack 3 and/or the width of the dental picks 1 and has a minimum depth which allows coating of the length of the coating on the dental pick 1 with a desired coating thickness.

Furthermore, an overflow 8 is provided beneath the surface 24 of the coating liquid 18 in the immersion bath container 7, allowing the displaced coating liquid 18 to overflow into a storage tank 9. This keeps the depth of the immersion bath constant.

According to FIG. 4, freshly prepared coating liquid 18 is regularly kept in the storage tank 9 to always keep the liquid level in the immersion tank container 7 constant by refilling the container from the storage tank 9 so that the length of the cleaning area 5 on the dental pick 1 remains essentially constant. The coating liquid 18 is first prepared in a container 9. Preparation includes heating the container 9 to about 100° C.; adding paraffin wax blocks, and melting at a temperature of between about 80° C. and about 100° C.; adding a liquid flavoring oil, preferably peppermint oil; adding emulsifiers and antioxidants; adding encapsulated flavoring oil, while agitating continuously by agitator 25 driven by electric motor 26, preferably spray-dried peppermint oil; dispersing the flavoring oils in the molten paraffin wax at a constant temperature of between about 75° C. and about 80° C.; and testing for homogeneous dispersion.

For filling and refilling the storage tank 9, the coating liquid 18 goes through a first inlet line 10, opened valves 29, 28, a circulating pump 11 and a second inlet line 12 into the immersion bath container 7. A drain valve 13, which can be connected to the inlet line 12 by the circulating pump 11, is situated beneath the bottom 27 of the immersion bath container 7. By opening the drain valve 13 and closing the valve 28 and turning on the circulating pump 11, the circulation of the coating liquid in the immersion bath container 7 is controlled and this also prevents flavoring substances in the coating liquid 18 from being able to settle at the bottom 27 of the immersion bath container 7. The inlet line valve 29 which is provided in the inlet line 10 is closed when the immersion container 7 is to be emptied. Then the valves 13, 28 and 15 are opened. If the storage tank 9 is to be emptied, the valves 15, 29 are opened and the valve 28 is closed. If the entire system is to be emptied, then all the valves 13, 28, 15 and 29 are opened.

The inlet lines 10, 12, 14 of the immersion bath 6 are heated jacketed water pipes (not shown here) in the present exemplary embodiment, preventing blockage due to deposited wax. The coating liquid 18 is completely replaced at regular intervals to prevent oxidation and contamination.

Again based on the flow chart in FIG. 1, there follows as the next step after the immersion bath 6 the transfer of the dental picks 1 to a drying zone for a post-heat treatment. Using a fan mechanism 19 situated above the dental picks 1, a hot stream of air 20 from a fan is blown out onto the dental picks 1 at a temperature of between about 90° C. and about 140° C., so that excess coating agent 18 and then later only due to the force of gravity and the action of the flow of air 20 from the fan, wax will run down to the tip 16 of the dental pick where a droplet (not shown here) develops and drips onto a bottom pan 22 arranged beneath the dental picks 1. Suitable air filters 30 are installed in the fan airstream 20 so that no dust or other particles of dirt will be blown onto the dental picks 1. In addition, the fan pressure and dwell time may be adjusted so that the incorporated substances come to lie freely at the surface while on the other hand all the drops of coating fluid are completely removed from the tip of the dental pick, or, in the case of a flosser (FIG. 6) from the strand of floss 44.

Finally, the dental picks 1 are placed in a cooling zone (not shown) where the coating 32 (FIG. 5) can cure at room temperature before dental picks 1 are removed from the conveyor rack 3 and packaged. After curing, the cleaning regions are relatively insensitive to soiling due to dust particles or the like.

Figure 5:
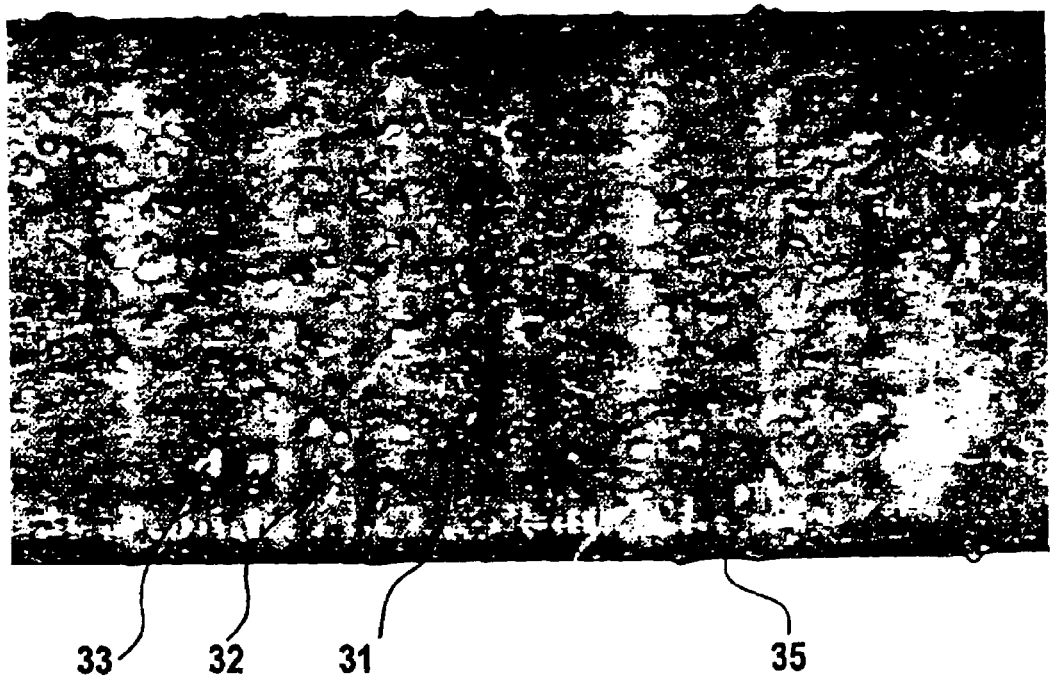
FIG. 5 a partial view in the direction Z according to FIG. 2 of the surface of a coating of a dental pick on a very large scale and
FIG. 6 a perspective view of a flosser with dental floss attached to both ends of the arms.

FIG. 5 shows on an enlarged scale a top view of the coating 32 according to this invention, showing clearly the solid encapsulated flavoring oils 33 as flavoring substances which are exposed here and have been freed of the wax 31. The wax 31 has thus been removed, i.e., thinned, in the areas where the flavoring substances 33 are easily discernible from the surface 34 of the coating 32 so that on coming in contact with saliva in the oral cavity (not shown), the encapsulated flavoring oils 33 are released immediately. Therefore, it is not necessary to first strip off the thick coating of wax from the surface of the dental pick in order to release the flavoring substances.

Figure 6:
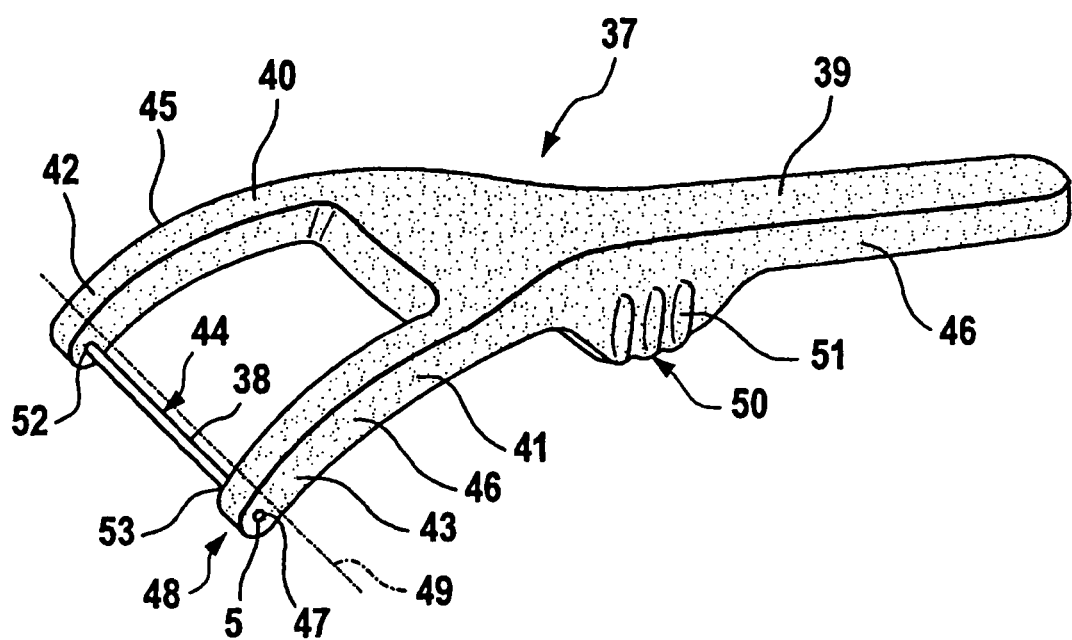

Finally, FIG. 6 shows a flosser 37 in a perspective view on an enlarged scale, consisting of a handle 39 which widens in the form of a fork at its one end via two arms 40, 41. A strand of dental floss 44 has been clamped at the free ends 42, 43 of the arms 40, 41, joining the two ends 42, 43 together. The strand of dental floss 44 passes through the free ends 42, 43 to the outside on both sides 45, 46, which is discernible by the circular cross section 47 on the side 46. An auxiliary line shown as a dash-dot line is also shown at the free ends 42, 43 running essentially parallel to the dental floss 44; this line should represent the extent to which the front free fork end 48 of the flosser 37 is inserted into the coating agent 18 in the immersion bath 7 according to FIG. 4.

Instead of the dental picks 1 attached to a sprue web 2 in FIG. 4, flossers 37 also attached to a sprue web (not shown here), like one of those shown in FIG. 6, is attached to the sprue receptacle 4 in such a way that the dental floss 44 is directed downward, with the dental floss 44 running essentially parallel to the surface of the coating agent 18 before the free fork end 48 is immersed into the bath up to the depth of immersion line 49 shown with a dotted line so that the dental floss 44 is coated by the coating agent 18. All other process steps such as those described previously for the dental pick 1 can also be applied appropriately to the flosser 37 according to FIG. 6.

According to FIG. 6 the flosser 37 has a gripping surface 50 on each side face 45, 46, widening at the lower end, with ribs 51 running from bottom to top provided on this gripping surface. It should also be pointed out here that the fan air flow in the process of drying the coating agent is always guided in such a way that it is directed toward one of the clamping points 52, 53 so that no unnecessary thickening occurs due to an accumulation of coating agent 18 in the cleaning area 38 which is between the two arms 40, 41 and ends shortly before the clamping points 52, 53, which would be of little advantage in the penetration of the dental floss 14 into an interdental space.

The invention claimed is:

1. A method for coating a cleaning region of an interdental cleaning device, comprising:
preheating the cleaning region to a predetermined temperature;
immersing the preheated cleaning region in a coating agent comprising a flavoring agent encapsulated in a wax, thereby forming a coating on the cleaning region;

forcing a flow of air across the coated cleaning region in a drip zone, thereby removing an excess portion of the wax and exposing at least a portion of the flavoring agent at a surface of the coating; and then cooling the cleaning region, thereby curing the coating, wherein the cleaning device comprises a flosser including a handle, a pair of arms extending outwardly from the handle forming a forked end, and a strand of dental floss stretched between the arms at the forked end defining the cleaning region, and wherein the handle serves as a conveyance and positioning aid for immersing the cleaning region in the coating agent.

2. The method according to claim 1, wherein the cleaning device comprises a dental pick, the dental pick including a clamping point disposed at a first end, and a tip disposed at an opposite end.

3. The method according to claim 2, wherein the cleaning device comprises a plurality of dental picks attached to a common web configured to aid in conveying and positioning the dental picks on an automatic conveyor.

4. The method according to claim 2, wherein the forced flow of air comprises hot air at a temperature in the range of about 90° C. to about 140° C. propelled in a longitudinal direction from the clamping point toward the tip.

5. The method according to claim 1, wherein the forced flow of air comprised hot air at a temperature in the range of about 90° C. to about 140° C. propelled in a longitudinal direction from the handle towards the strand of dental floss.

6. The method according to claim 1, wherein the predetermined temperature is in the range of about 40° C. to about 100° C.

7. The method according to claim 1, wherein immersing the cleaning region in a coating agent comprises circulating the coating agent at a temperature of about 70° C. to about 90° C. in an immersion bath container.

8. The method according to claim 1, wherein the cleaning region is cooled to about ambient temperature.

9. The method according to claim 1, wherein the coating agent further comprises a second flavoring agent in a liquid state.

10. The method according to claim 9, wherein the coating agent includes:

between about 50 percent and about 75 percent paraffin wax;

between about 20 percent and about 40 percent wax encapsulated flavoring agent;

between about 2 percent and about 6 percent liquid flavoring agent; and between about 0.1 percent to about 5 percent additives, the additives including an emulsifier and an antioxidant.

11. The method according to claim 10, wherein the additives include 2,6-di-tert-butyl-4-methylphenol.

12. The method according to claim 10, further comprising preparing the coating agent in an agitator prior to immersing the cleaning region in the coating agent, wherein preparing the coating agent comprises:

heating an immersion bath container to about 100° C.;

adding one or more paraffin wax blocks and melting the blocks at a temperature of between about 80° C. and about 100° C.;

adding the liquid flavoring agent;

adding the additives;

adding the wax encapsulated flavoring agent;

agitating the liquid and wax encapsulated flavoring agents to facilitate dispersion of the flavoring agents in the paraffin wax at a constant temperature of about 75° C. to about 80° C.; and testing for homogeneous dispersion of the flavoring agents.

13. The method according to claim 12, wherein the liquid flavoring agent comprises peppermint oil.

14. The method according to claim 12, wherein the wax encapsulated flavoring agent comprises spray-dried peppermint oil.

* * * * *

UNITED STATES PATENT AND TRADEMARK OFFICE
CERTIFICATE OF CORRECTION

| | | |
|---|---|---|
| PATENT NO. | : 7,579,039 B2 | Page 1 of 1 |
| APPLICATION NO. | : 10/558161 | |
| DATED | : August 25, 2009 | |
| INVENTOR(S) | : Gerhard Finger, Thorsten Emge and Manfred Klawuhn | |

It is certified that error appears in the above-identified patent and that said Letters Patent is hereby corrected as shown below:

Col. 9, claim 5, line 27, delete "comprised" and insert -- comprises --.

Signed and Sealed this

Third Day of November, 2009

David J. Kappos
*Director of the United States Patent and Trademark Office*

UNITED STATES PATENT AND TRADEMARK OFFICE
CERTIFICATE OF CORRECTION

PATENT NO.       : 7,579,039 B2                                    Page 1 of 1
APPLICATION NO. : 10/558161
DATED            : August 25, 2009
INVENTOR(S)      : Finger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 601 days.

Signed and Sealed this

Fourteenth Day of December, 2010

David J. Kappos
*Director of the United States Patent and Trademark Office*